US006440101B1

(12) United States Patent
Grabenkort et al.

(10) Patent No.: US 6,440,101 B1
(45) Date of Patent: Aug. 27, 2002

(54) SYRINGE SYSTEMS FOR LYOPHILIZED DRUGS AND METHODS FOR MAKING THE SAME

(75) Inventors: Richard W. Grabenkort, Barrington; Randall M. Farmer, Mundelein, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 99 days.

(21) Appl. No.: 09/584,307

(22) Filed: May 31, 2000

(51) Int. Cl.[7] .............................................. A61M 37/00
(52) U.S. Cl. ............................ 604/89; 604/82; 604/87; 604/122
(58) Field of Search ............................ 604/82, 85, 84, 604/86, 87, 89, 92, 122, 191, 231

(56) References Cited

U.S. PATENT DOCUMENTS

| | | | |
|---|---|---|---|
| 3,810,469 A | | 5/1974 | Hurschman |
| 4,254,768 A | | 3/1981 | Ty |
| 4,506,455 A | | 3/1985 | Rossi |
| 4,693,706 A | * | 9/1987 | Ennis, III .................. 604/87 |
| 5,435,076 A | | 7/1995 | Hjertman et al. |
| 5,531,683 A | * | 7/1996 | Kriesel et al. .............. 604/89 |
| 5,643,218 A | * | 7/1997 | Lynn et al. ................ 604/191 |
| 5,685,846 A | * | 11/1997 | Michaels, Jr. .............. 604/82 |
| 5,697,915 A | * | 12/1997 | Lynn ........................ 604/191 |
| 5,709,666 A | * | 1/1998 | Reynolds .................. 604/191 |
| 5,743,886 A | * | 4/1998 | Lynn et al. ................ 604/191 |
| 5,769,825 A | * | 6/1998 | Lynn ........................ 604/191 |
| 5,779,668 A | | 7/1998 | Grabenkort |
| 5,788,670 A | * | 8/1998 | Reinhard et al. ............ 604/89 |
| 5,833,653 A | * | 11/1998 | Vetter et al. ................ 604/82 |
| 5,865,803 A | * | 2/1999 | Major ...................... 604/122 |
| 5,971,953 A | * | 10/1999 | Bachynsky ................. 604/89 |

* cited by examiner

Primary Examiner—Teresa Walberg
Assistant Examiner—Fadi H. Dahbour
(74) Attorney, Agent, or Firm—Beth A. Vrioni

(57) ABSTRACT

A syringe system requires a decreased vertical travel for sealing during a lyophilization process and therefore provides for increased utilization of space in a lyophilization chamber. The syringe system is provided with a sterility maintenance sleeve including a stopper affixed thereto for sealingly engaging the syringe barrel to define a drug chamber. The sterility maintenance sleeve is provided with a venting passage to permit egress of vapor from the drug chamber during lyophilization. A plug cap cooperating with the sterility maintenance sleeve includes an occluding tip which is adapted to occupy the venting passage and seal the drug chamber after lyophilization. The plug cap is provided with a support structure in the form of flexible fins for supporting the plug cap in a venting position in which the occluding tip is removed from the venting passage to permit egress of drug solution vapor from the drug chamber during lyophilization. After lyophilization, the plug cap is moved into a sealing position in which the drug chamber is sealed against contamination.

35 Claims, 8 Drawing Sheets

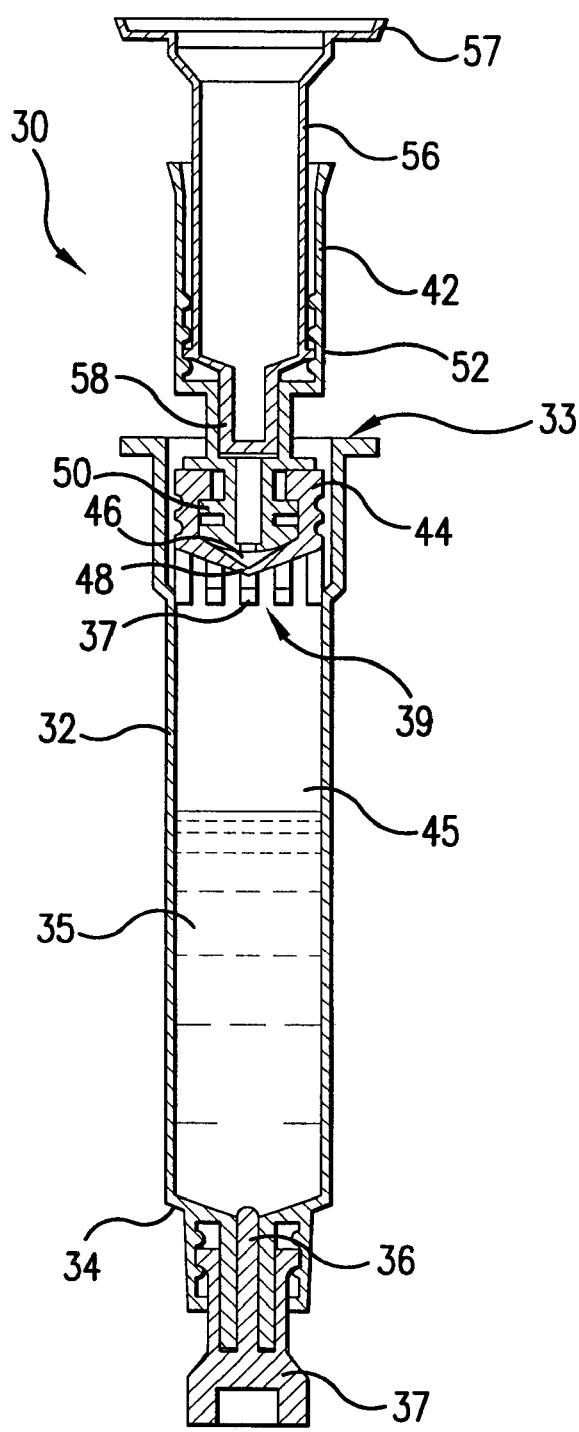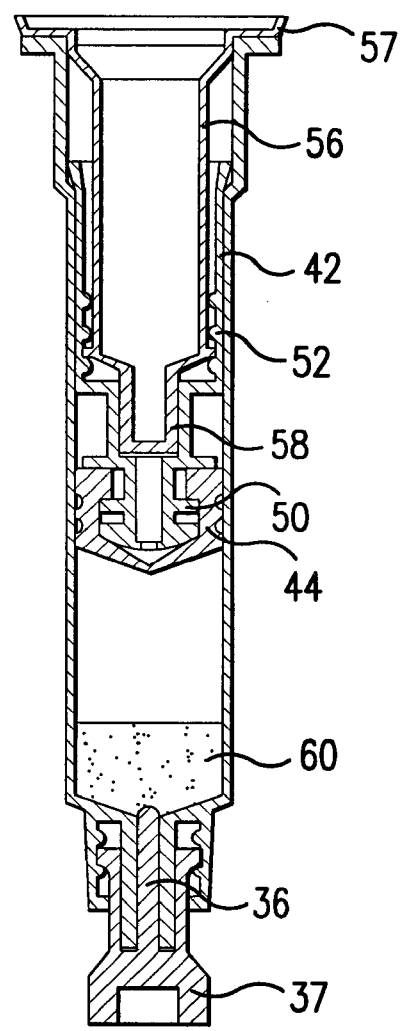
FIG.2
PRIOR ART
FIG.3
PRIOR ART

SYRINGE SYSTEMS FOR LYOPHILIZED DRUGS AND METHODS FOR MAKING THE SAME

TECHNICAL FIELD

This invention relates generally to syringe systems that are suitable for packaging, mixing and delivering a medical solution formed by mixing a dry, lyophilized drug component with a liquid diluent. More specifically, the invention relates to syringe systems that permit lyophilization of a drug solution contained therein. The invention also relates to methods of making such syringe systems.

BACKGROUND OF THE INVENTION AND TECHNICAL PROBLEMS POSED BY THE PRIOR ART

Generally, lyophilization is a process by which the volatile components, such as solvents including water, are removed from a substance. Certain substances, especially pharmaceutical substances, are more stable over time if the volatile components are removed. Since lyophilized drugs are typically more stable, have longer shelf life, have more reliable purity and are easier to store and transport than other formulations, lyophilization has become commonplace in the pharmaceutical industry.

It is known to provide "wet/dry" drug mixing and delivery products that utilize a primary syringe system, containing a lyophilized drug, and a secondary syringe system that contains a diluent used to reconstitute the lyophilized drug. When the drug is to be administered to a patient, the secondary syringe system is inserted into the primary syringe system and the diluent is dispensed into the primary syringe barrel to reconstitute the lyophilized drug. These "wet/dry" syringe systems are useful in pharmaceutical applications where pre-mixed solutions or suspensions of a drug are not stable enough to withstand prolonged periods of storage. Such systems are disclosed in U.S. Pat. No. 5,779,668, the subject matter and entire writing of which is incorporated herein by reference.

Typically, the manufacture of the primary syringe system containing the lyophilized drug involves mass processing of a number of syringe systems in a lyophilization chamber. Prior art lyophilization chambers are exemplified by FIG. 1 and U.S. Pat. No. 4,506,455, the subject matter and entire writing of which is incorporated herein by reference. The lyophilization chamber 10 generally comprises a chamber wall 12 which is manufactured to provide insulation during the lyophilization process. Enclosed within the wall 12 are a series of shelves 14 which are adapted to move relative to one another and which include implements, such as refrigeration and heating coils, for raising and lowering the temperature of the shelves. A hydraulic actuator 18 moves the top shelf upward, creating a space between the top shelf and the adjacent second shelf, and a number of syringe systems 22, supported on trays or "pucks" 20 are loaded onto the second shelf. The containers or trays 20 are typically transported on a transport carriage 26 and slid across a loading table 24 such that the trays can be loaded onto the respective shelves 14. The top shelf and second shelf are then raised and syringe systems 22 are loaded onto the third shelf. This loading sequence is repeated until the upright syringe systems 22 occupy the spaces between the shelves 14. Once fully loaded, the chamber door 19 is closed and the interior subjected to a lyophilization process which may typically take a number of days to complete. After the lyophilization process is complete, the top shelf is lowered and the shelves are collapsed towards one another such that movement of the shelves causes a collapse and therefore sealing of the syringe systems 22 in a manner that will be described below.

Typical lyophilization processes involve two stages. In the first stage, the drug solution is subjected to low temperatures, typically −50 (C) and completely frozen to separate the water or other solvent from the solute ingredients. In the second stage, the water or other solvent is separated from the frozen product by heating the contents slowly, under carefully controlled conditions, and under high vacuum so that the solvent leaves the products through sublimation. Drying is accomplished as the frozen solvent is transformed into vapor. This vapor migrates through the crystallized drug and escapes from the syringe system through a venting system.

FIGS. 2 and 3 illustrate a prior art syringe system for permitting venting of the drug during lyophilization. During the lyophilization process, the syringe system 30 is maintained in an upright position in a metal holder or puck (not shown). FIG. 2 illustrates the syringe system 30 configured in a venting position. The syringe system 30 comprises a generally cylindrical syringe barrel 32 which includes an open end 33 and a closed end 34. The closed end 34 includes a delivery passage 36 which is later used for delivery of the mixed drug from the syringe system 30. During lyophilization, the delivery passage 36 is sealed by a closure 37 and the syringe barrel 32 contains a drug solution 35.

In accordance with prior art syringe systems, venting is provided by a series of venting channels 39 which are formed in the syringe barrel 32 near the open end 33. These channels are formed between a series of ribs 37 that are integrally molded with the syringe barrel 32. The syringe system 30 also includes a sterility maintenance sleeve 42 and plug cap 56 which are intended to seal the interior of the syringe barrel 32 against contamination once the syringe is moved into its sealed position as shown in FIG. 3. The sterility maintenance sleeve 42 includes a large diameter portion 52 from which extends a stopper retaining head 50 that is shaped to resiliently retain a rubber stopper 44 thereon. Stopper 44 is adapted to sealingly engage the interior surface of the syringe 32 and, in the venting position as shown in FIG. 2, abuts the ribs 37 thereby permitting egress of vapor through the channels 39 from the drug chamber 45 of the syringe 32.

FIG. 3 illustrates the syringe system 30 configured in a sealing position after the lyophilization process has been performed. The sterility maintenance sleeve 42 and plug cap 56 are moved to the sealing position in which the stopper 44 is located further into the syringe 32 and a sealing head 57 of the plug cap 56 engages the syringe 32. As will be recognized by those of ordinary skill in the art, the plug cap and sterility maintenance sleeve 42 are moved to the sealing position from the venting position by movement of the shelves in the lyophilization chamber.

Prior art syringe systems require a rather extensive vertical travel of the sealing components when moving from a venting position to a sealing position. This travel dimension places limits on the capacity of the lyophilization chamber since the shelves must be spaced to accommodate the syringe system when it is configured in the venting position. Since lyophilization processes may take several days for some pharmaceutical substances, space within the lyophilization chamber—typically a very expensive piece of equipment—is at a premium. It would therefore be desirable to provide a syringe system which requires less vertical movement for sealing compared to prior art syringe systems. Such a system would permit more efficient use of the space within the lyophilization chamber.

The venting techniques of prior art syringe systems are also disadvantageous in that they do not provide an efficient flow path for drug solution vapor during the drying steps of lyophilization. More specifically, the fluid path that vapor must travel to escape from the drug chamber to the ambient surroundings during lyophilization is somewhat restricted, since the venting passages are formed by the engagement of a resilient stopper with channels formed in the syringe barrel. It would therefore be desirable to provide a syringe system which provides an efficient flow path for drug solution vapors during lyophilization, thereby decreasing the time required for drying during lyophilization.

SUMMARY OF THE INVENTION

The benefits and advantages described above are realized by the present invention which provides a syringe system that requires a decreased vertical travel when changing from a venting configuration to sealing configuration. In a preferred embodiment, the invention provides a syringe system including a syringe barrel having an open end and an opposite dispensing end, a sterility maintenance sleeve cooperating with the syringe barrel and including a sleeve barrel having an interior space, a stopper affixed thereto for sealingly engaging the syringe barrel to define a drug chamber for containing drug solution, and a venting passage formed in the sterility maintenance sleeve and the stopper in order to permit egress of drug solution vapor from the drug chamber during the lyophilization process. A plug cap is cooperatively associated with the sterility maintenance sleeve and provided with an occluding tip for sealing the venting passage. The sterility maintenance sleeve may be initially inserted to an installed position, where the stopper is disposed further into the syringe barrel compared to prior art devices and thus the overall height of the syringe system in the venting configuration is reduced.

The occluding tip is preferably configured to permit adequate flow of vapor through the venting passage for efficient drying during the lyophilization process. Specifically, the occluding tip is provided with a tapered end which is dimensioned so as to provide an annular flow passage with the venting passage formed in the sterility maintenance sleeve. The occluding tip is adapted to occupy, in the venting position, an enlarged diameter portion of the venting passage, for example, a female threaded portion for later receiving a male threaded portion of a diluent syringe. The shape of the flow passage for vapors from the drug solution is therefore less restrictive than prior art devices and thus provides for more efficient and quicker lyophilization.

The plug cap is preferably provided with a support structure in the form of flexible fins that extend outward from a central portion. The fins function to frictionally engage an interior surface of the sterility maintenance sleeve to support the plug cap in the venting position. The fins are flexible enough to deform and thereby permit the plug cap to move within the sterility maintenance sleeve upon application of a force to the plug cap without causing movement of the sterility maintenance sleeve within the syringe barrel. The fins also provide, in conjunction with the interior surface of the sterility maintenance sleeve, large flow passages for drug solution vapor, thereby providing for more efficient drying and vapor egress from the drug chamber during lyophilization.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 2 is a sectional view of a prior art syringe system in a venting position as described above;

FIG. 3 is a sectional view of a prior art syringe system in a sealed position as described above;

DETAILED DESCRIPTION OF THE PREFERRED EMBODIMENT

While this invention is susceptible of embodiment in many different forms, this specification and the accompanying drawings disclose only some specific forms as examples of the invention. The invention is not intended to be limited to the embodiments so described. The scope of the invention is pointed out in the appended claims. Figures illustrating the apparatus show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Figure 1:
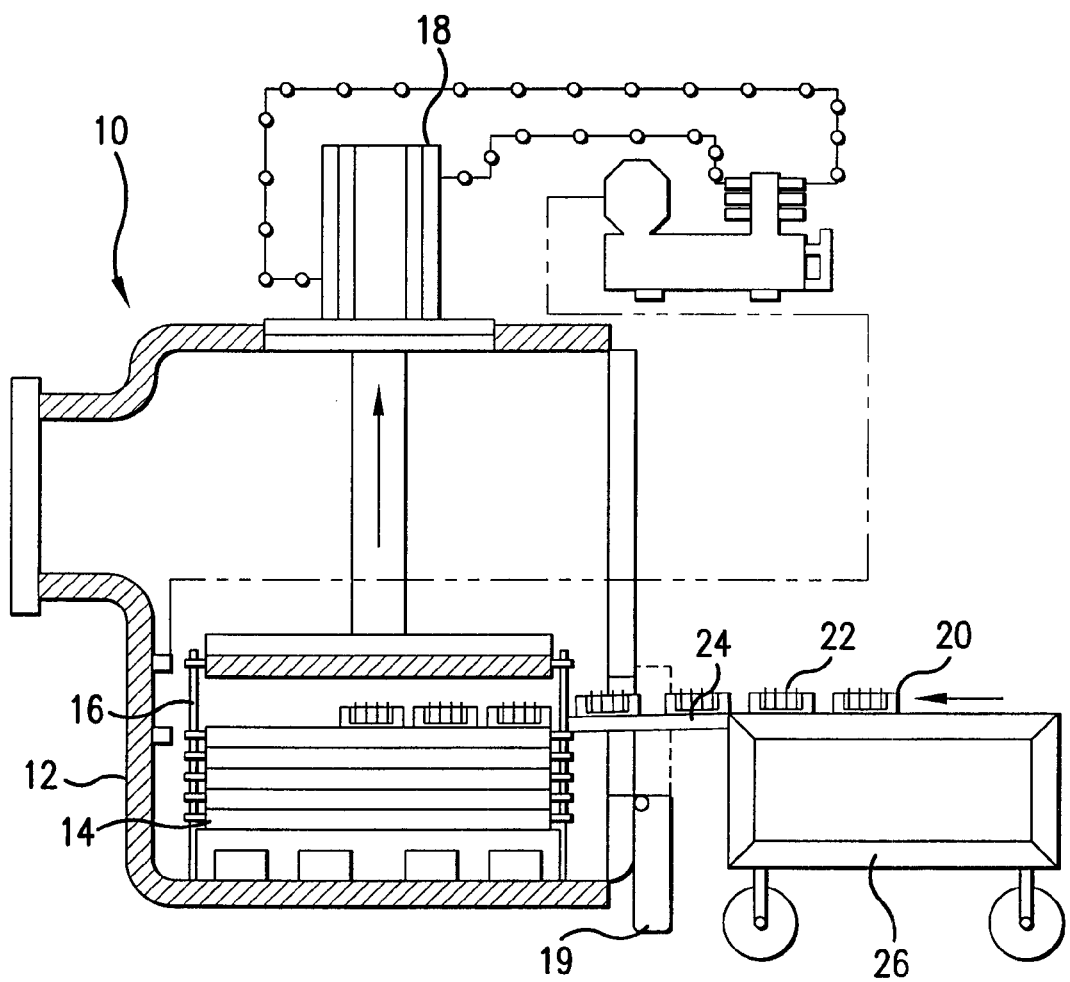
FIG. 1 is a schematic diagram of a lyophilization chamber and loading apparatus according to the prior art as described above.
Figure 4:
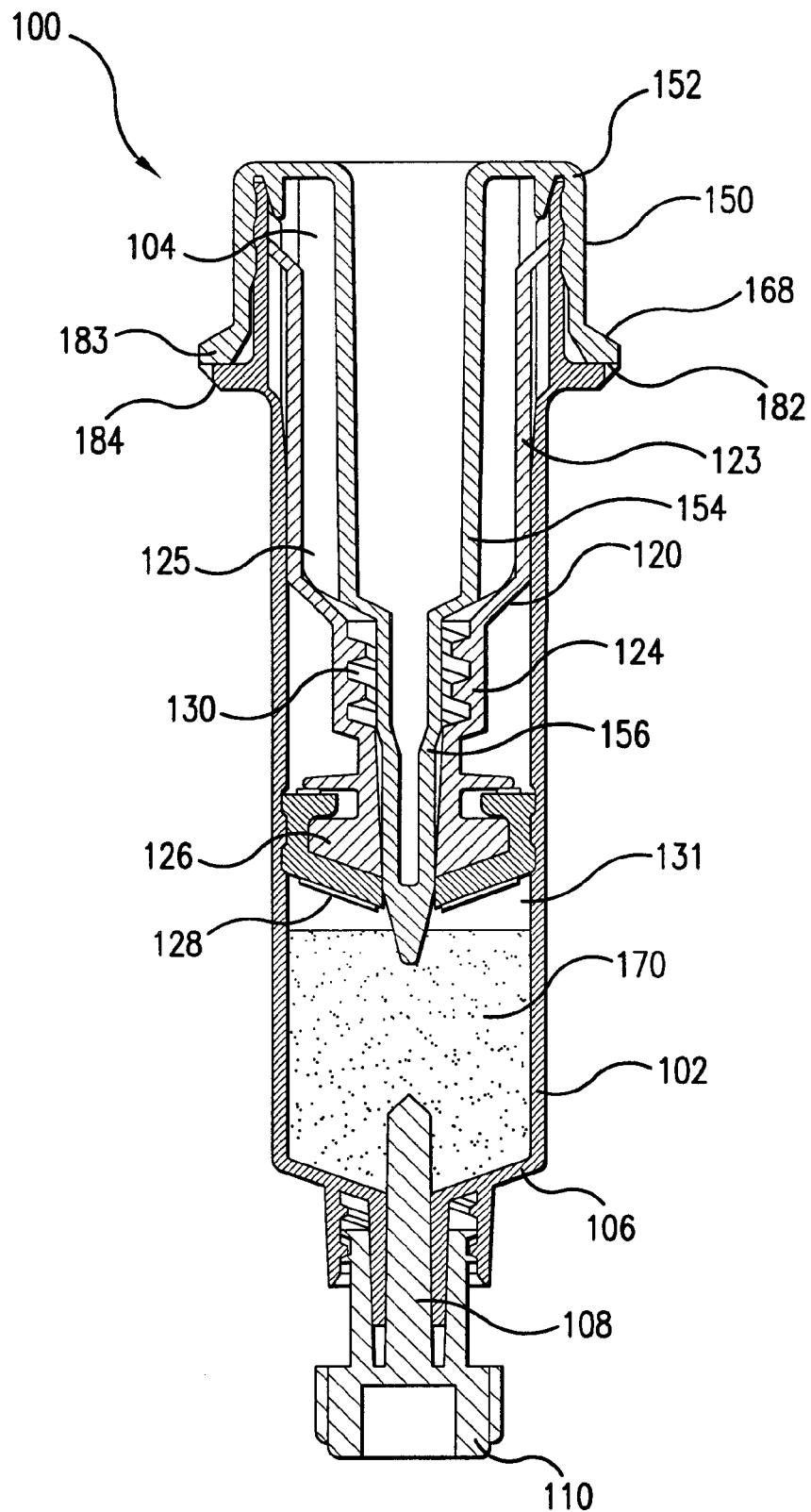
FIG. 4 is sectional view of an assembled exemplary syringe system according to a preferred embodiment of the present invention.

Referring now to FIG. 4, there is illustrated an exemplary assembled syringe system according to the invention. The syringe system, generally referenced with the number 100, includes a primary syringe barrel 102 which has an open end 104 and a closed end 106 opposite to the open end 104. Closed end 106 includes a delivery passage 108 for permitting later delivery of the mixed drug from the syringe barrel 102. A closure 110 is provided in the dispensing passage in order to seal the interior of the syringe during the lyophilization process. The syringe system 100 also includes a sterility maintenance sleeve 120 for sealing the syringe barrel 102 against contamination after the lyophilization process is complete. The sterility maintenance sleeve 120 includes a generally cylindrical sleeve barrel 123 which extends into a round stopper head 126 for retaining a cylindrical stopper 128 resiliently thereon. The stopper 128 and closed end 106 of the syringe barrel 102 define a drug chamber 131 containing a lyophilized drug 170. The sterility maintenance sleeve 120 also includes a female threaded portion 124 for receiving a male threaded connector on a diluent syringe (not shown) for mixing the lyophilized drug just prior to delivery to a patient.

A venting passage 130 extends within the sterility maintenance sleeve 120 and through the stopper retaining head 126 and female threaded portion 124 to the interior space 125 of the sleeve barrel 123. The venting passage 131 also includes a generally circular stopper passage 132 formed in the stopper 128 and aligned with the portion of the venting passage 131 that extends through the stopper retaining head 126.

A plug cap 150 is disposed within the sleeve barrel 123 of the sterility maintenance sleeve 120 for sealing the syringe system 100. The plug cap includes a generally cylindrical central portion 154, a cap portion 152 for sealing the open end 104 of the syringe barrel 102 and an occluding tip 156 extending from the central portion 154. The occluding tip 156 occupies and seals the venting passage 130 in a manner that will be explained in more detail below. The cap portion 152 of the plug cap 150 is adapted to seal the open end 104 of the syringe barrel and receive a shrink band 168. An annular sealing face 182 is provided on a flange 183 that engages a shoulder 184 formed on the syringe barrel 102. The shrink band is applied around the flange 183 and shoulder 184 to seal and fasten the plug cap 150 to the syringe barrel 102.

Figure 5:
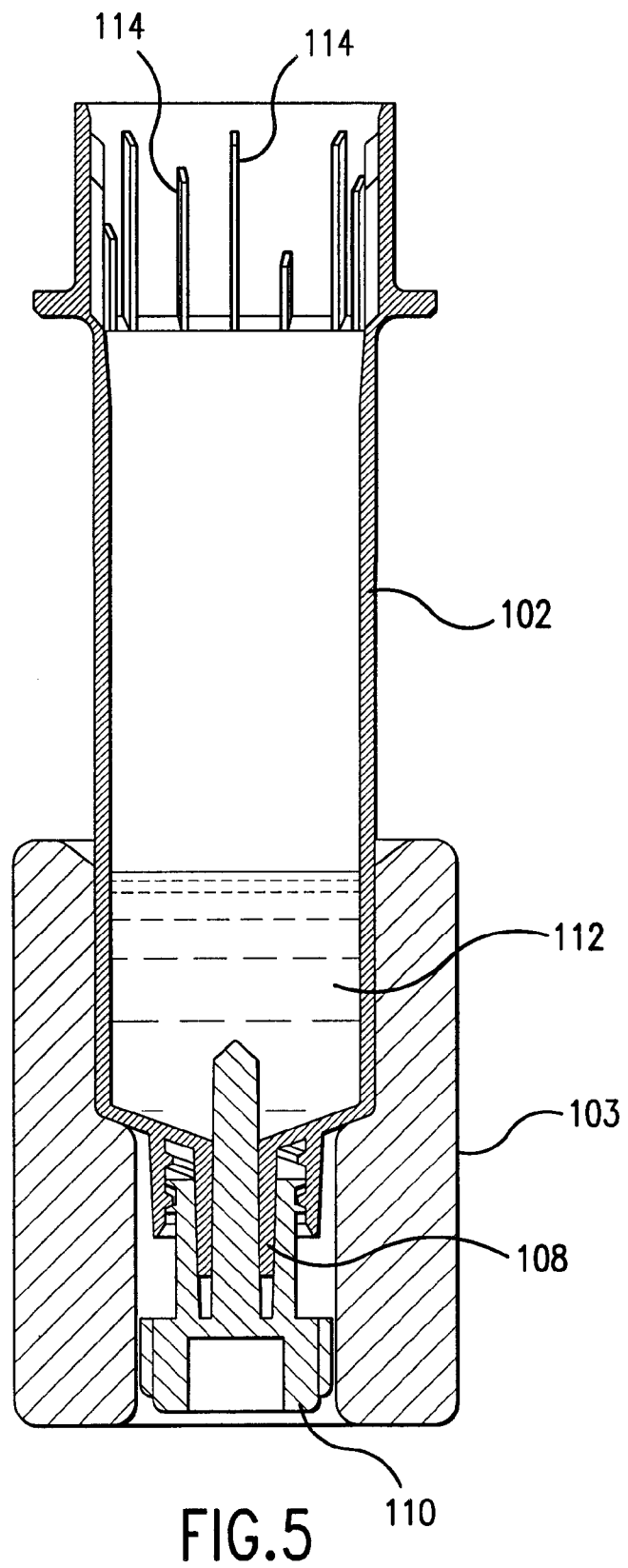
FIG. 5 is a sectional view illustrating a puck and barrel sub-assembly of an exemplary syringe system according to the invention.

An exemplary method of making a syringe system according to the invention will now be described with reference to FIGS. 5–8. FIG. 5 illustrates a sub-assembly of an exemplary syringe system according to the invention. The syringe barrel 102, including the closure 110 sealing the delivery passage 108, contains drug solution 112 and is provided in a holder or puck 103, as is known in the art, for maintaining the syringe barrel 102 in an upright position on the shelf of the lyophilization chamber. The puck 103 is preferably made of a metallic material, such as aluminum, suitable for heat conduction and advantageous in the conduction of heat to and away from the drug solution 112. The primary syringe barrel 102 includes a plurality of guiding projections 114 formed near the open end 104 and integral with the syringe barrel 102. The guiding projections 114 function to support the sterility maintenance sleeve during installation as will be explained. The guiding projections 114 also function to prevent rotation of the sterility maintenance sleeve during installation and during later use of the syringe system 100 with a diluent syringe for reconstituting the lyophilized drug. The guiding projections 114 preferably are designed to be of variable lengths.

Figure 6:
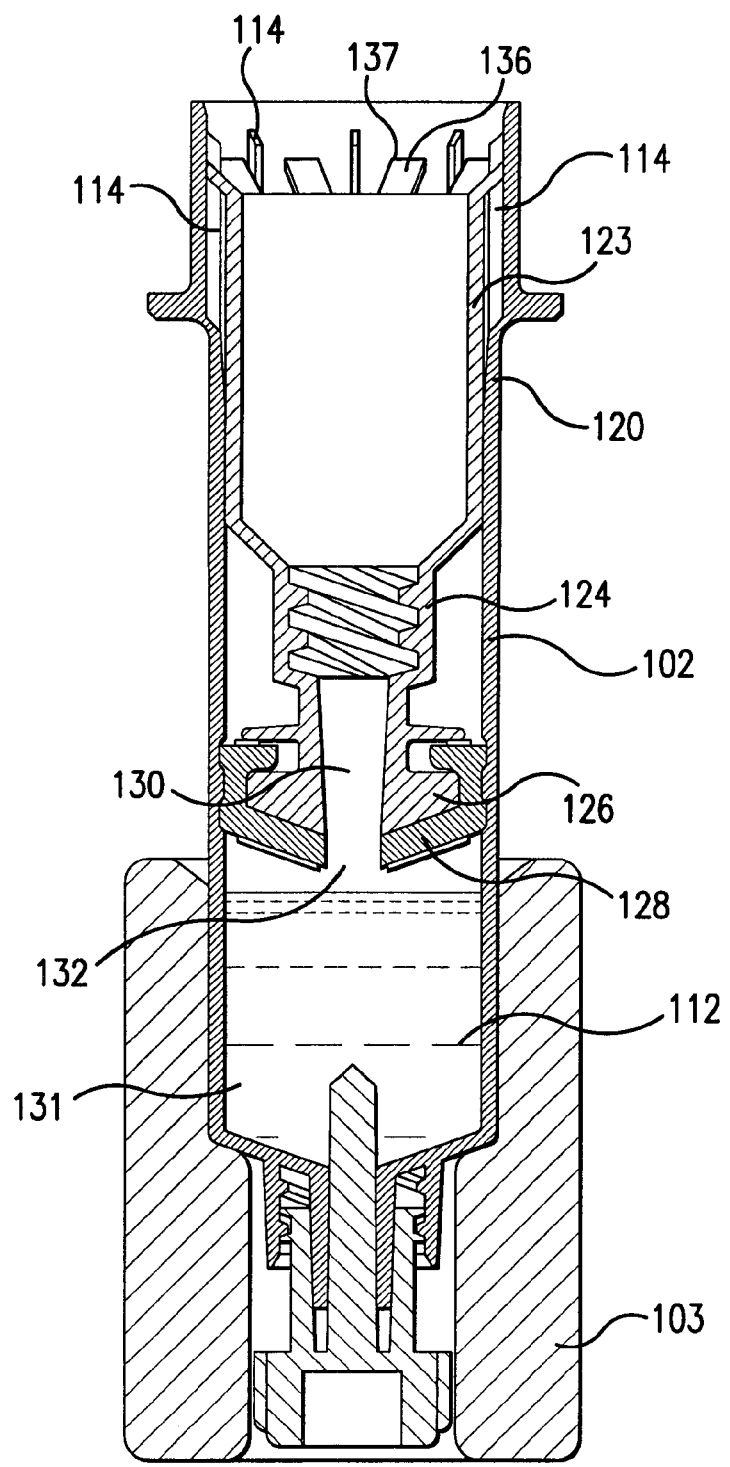
FIG. 6 is a sectional view illustrating the sub-assembly of FIG. 5 and an added exemplary sterility sleeve according to the present invention.

FIG. 6 illustrates a step of providing the sterility maintenance sleeve 120 in the sub-assembly described above relative to FIG. 5. The sterility maintenance sleeve 120 is inserted into the syringe barrel 102 to an installed position as shown. The sterility maintenance sleeve 120 includes a number of radially projecting tabs 136 which extend outward from the sleeve barrel 123. Projecting tabs 136 also extend in an angled upward direction away from the sleeve barrel 123. The projecting tabs 136 function to maintain the sterility maintenance sleeve in position, as the projecting tabs 136 rest on the tops of the shorter guiding projections 114 and are disposed between the longer guiding projections 114. Projecting tabs 136 also function to prevent the sterility maintenance sleeve 120 from rotating relative to the syringe barrel 102, particularly when the diluent syringe is later connected to the syringe system 100 using the female threaded connector 124 and an associated male threaded connector on the diluent syringe (not shown). Moreover, the projecting tabs 136 are adapted to flex or bend, or may be frangibly connected to the sleeve barrel 123 to permit the sterility maintenance sleeve to be inserted further down into the syringe barrel 102 as may be needed for the stopper 128 to later displace and dispense reconstituted drug.

Note that the projecting tabs 136 engage the guiding projections 114 at different points along the inside of the sleeve barrel 123 because of the variable lengths of the projections 114. This ensures that the force required to initially push the sleeve barrel 123 within the syringe barrel 102 is reduced.

As illustrated, in this exemplary embodiment, the stopper 128 is located approximately two-thirds into the depth of the syringe barrel 102 when the sterility maintenance sleeve 120 is in the installed position, in which the sterility maintenance sleeve 120, including its top end 137, defined by the ends of projecting tabs 136, is disposed completely within the syringe barrel 102. Those of ordinary skill will recognize, however, that the specific position of the stopper 128, when the sterility maintenance sleeve 102 is in the installed position, will vary depending on the amount of drug solution 112 contained in the syringe barrel 102. The stopper 128 sealingly engages an interior surface of the syringe barrel 102. Preferably, the sleeve barrel 123 of the sterility maintenance sleeve 120 is dimensioned to provide a firm seal against the inside surface of the syringe barrel 102, yet permit reciprocal movement within and with respect to the syringe barrel 102 when the syringe system 100 is later used with a diluent syringe to reconstitute the lyophilized drug.

In accordance with a primary aspect of the invention, the sterility maintenance sleeve 120 is provided with a venting passage 130 of a generally circular cross-section that extends through the female threaded portion 124 and the stopper retaining head 126 and which includes a stopper passage 132 formed on the stopper 128. The venting passage 130 permits egress of drug solution vapors produced in the drug chamber 131 during the drying stage of lyophilization. As will be recognized by those of ordinary skill, in contrast to prior art syringe systems, venting is permitted with the sterility maintenance sleeve in the installed position shown in FIG. 6.

Figure 7:
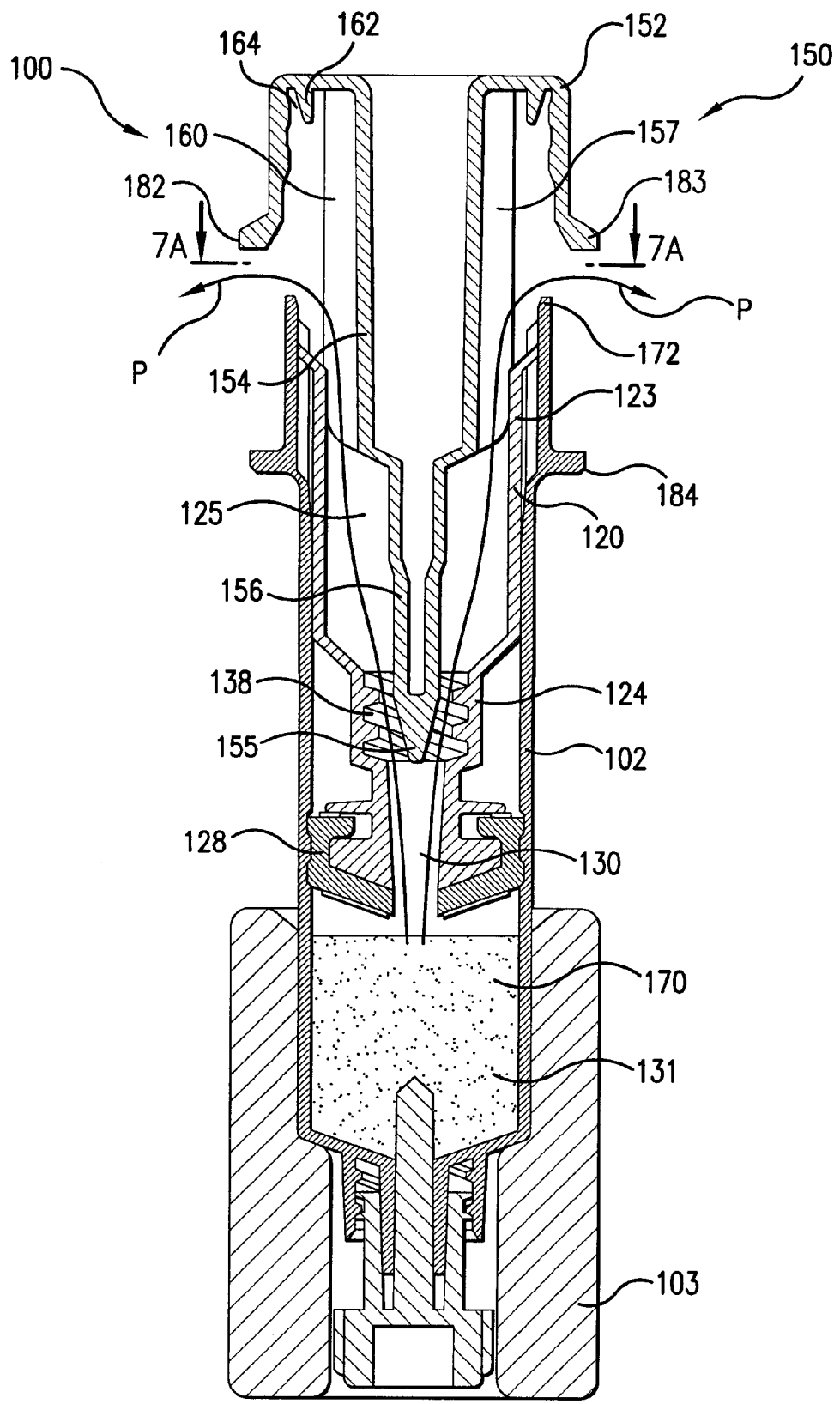
FIG. 7 is a sectional view illustrating the sub-assembly of FIG. 6 and an added exemplary plug cap disposed in an evacuation position according to the present invention.

FIG. 7 illustrates a step of inserting a plug cap 150 into the sterility maintenance sleeve 120 according to the invention. Prior to insertion of the syringe system 100 into the lyophilization chamber, the plug cap 150 is inserted into the sleeve barrel 123 at a venting position as shown to permit venting and later sealing of the syringe system 100. The plug cap 150 includes a generally cylindrical cap portion 152, a generally cylindrical central portion 154 and an occluding tip 156. The occluding tip 156 is adapted to fit within the venting passage 130 to prevent fluid passage therein and thereby seal the drug chamber 131 against contamination. The occluding tip 156 is generally cylindrical in shape and includes a tapered tip 155 which functions to initially guide the occluding tip 156 into the venting passage and to engage a resilient lip seal 129 formed on the stopper 128.

Figure 7A:
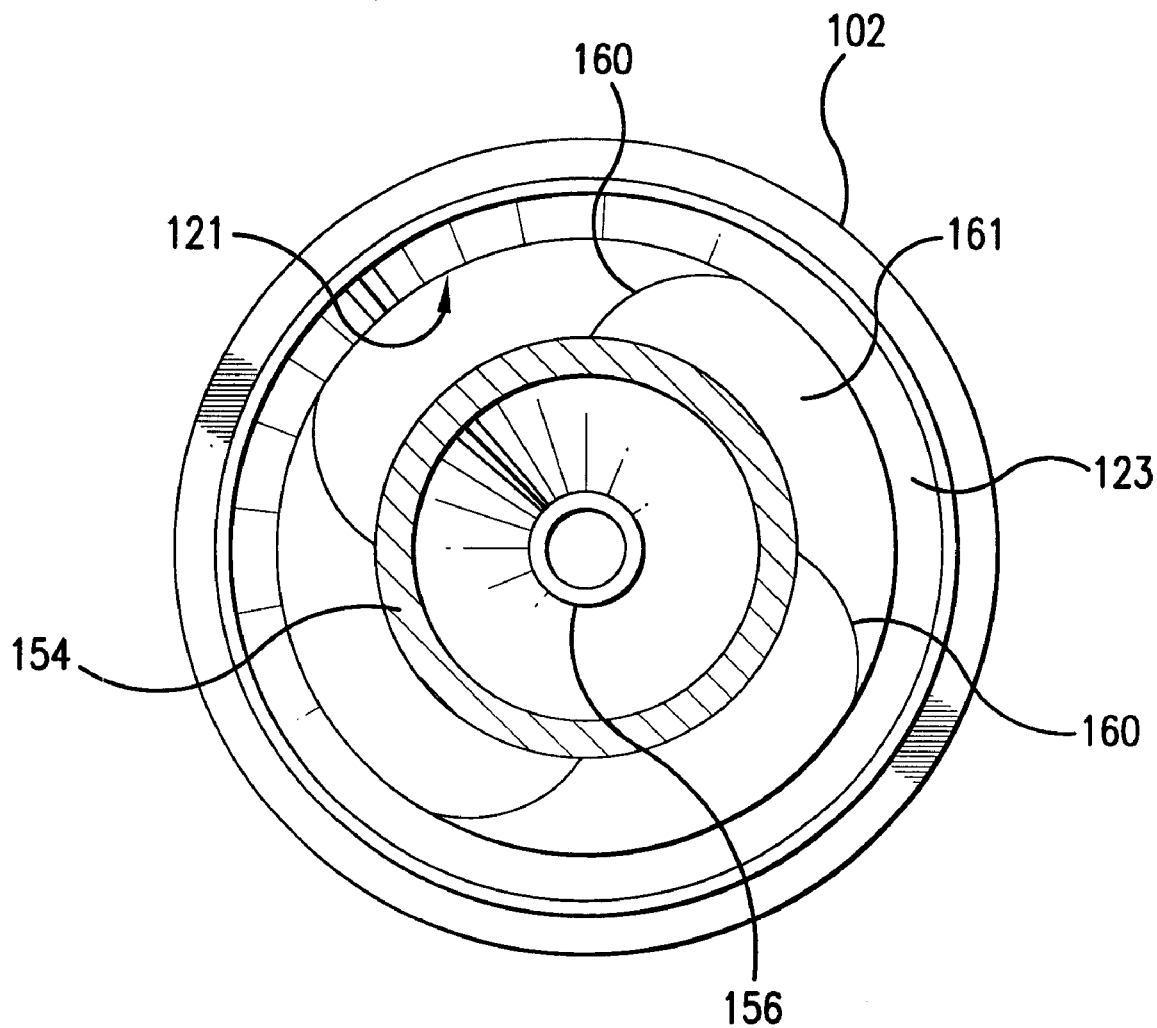
FIG. 7A is a cross-section view taken in reference to line 7A—7A in FIG. 7.

According to another primary aspect of the invention, the plug cap 150 is provided with a support structure 157 for supporting the plug cap in the venting position. In a preferred embodiment, the support structure is provided as four flexible projecting fins 160 extending outward from the central portion 154 of the plug cap 150 (only 2 fins are shown in FIG. 7). Referring additionally to FIG. 7A, which is a cross-section in reference to line 7A—7A in FIG. 7, the projecting fins 160 preferably extend in a non-radial direction from the central axis of the plug cap 150 SO as to facilitate bending or deformation when the plug cap 150 is inserted into the sleeve barrel 150. The support structure 157 supports the plug cap 150 in the venting position as the fins 160 frictionally engage an interior surface 121 of the sleeve barrel 123. The fins 160 form interstitial passages 161 with the interior surface 121 of the sleeve barrel 123 for permitting egress of the drug solution vapors from the interior space of the barrel sleeve 123 to the ambient surroundings of the syringe system 100.

According to another primary aspect of the invention, the occluding tip 156 of the plug cap 150 is positioned just inside the enlarged portion 138 of the venting passage 130 in the female threaded portion 124 when the plug cap 150 is in the venting position. In this manner, as will be recognized by those of ordinary skill, a generally annular flow passage is formed by the occluding tip 156 and the internal surface of the female threaded portion 124. Moreover, the size of the annular passage is such that the flow area is equal to or greater than the flow area provided by the passage through the stopper retaining head 126 so as to provide an unrestricted flow path (P) for egress of vapor from the drug chamber 131. Similarly, the flow path provided between the fins 160 of the plug cap 150 and the barrel sleeve 123 provides a flow area that is equal to or greater than the flow area between the occluding tip 156 and the female threaded portion 124 so as to provide unrestricted egress of vapor and efficient drying during the lyophilization process.

Also in accordance with another aspect of the invention, the cap portion 152 of the plug cap 150 is provided with structure for sealing the open end 104 of the syringe barrel 102. Specifically, in this exemplary embodiment, the cap portion 152 is provided with an annular projecting lip 162 which extends from the cap portion 152 in an axial direction and forms an annular recess 164 for receiving the lip 172 formed on the upper end of the syringe barrel 102.

In accordance with the advantageous aspects of the present invention, the vertical height of the syringe system 100, configured in the venting position, is reduced compared to prior art devices. In contrast to the prior art devices, the stopper 128 need not be oriented at the top of the syringe barrel 102 in order for venting to occur. Rather, the stopper and sterility maintenance sleeve 120 may be oriented in the installed position while still permitting venting of the drug chamber 131.

Figure 8:
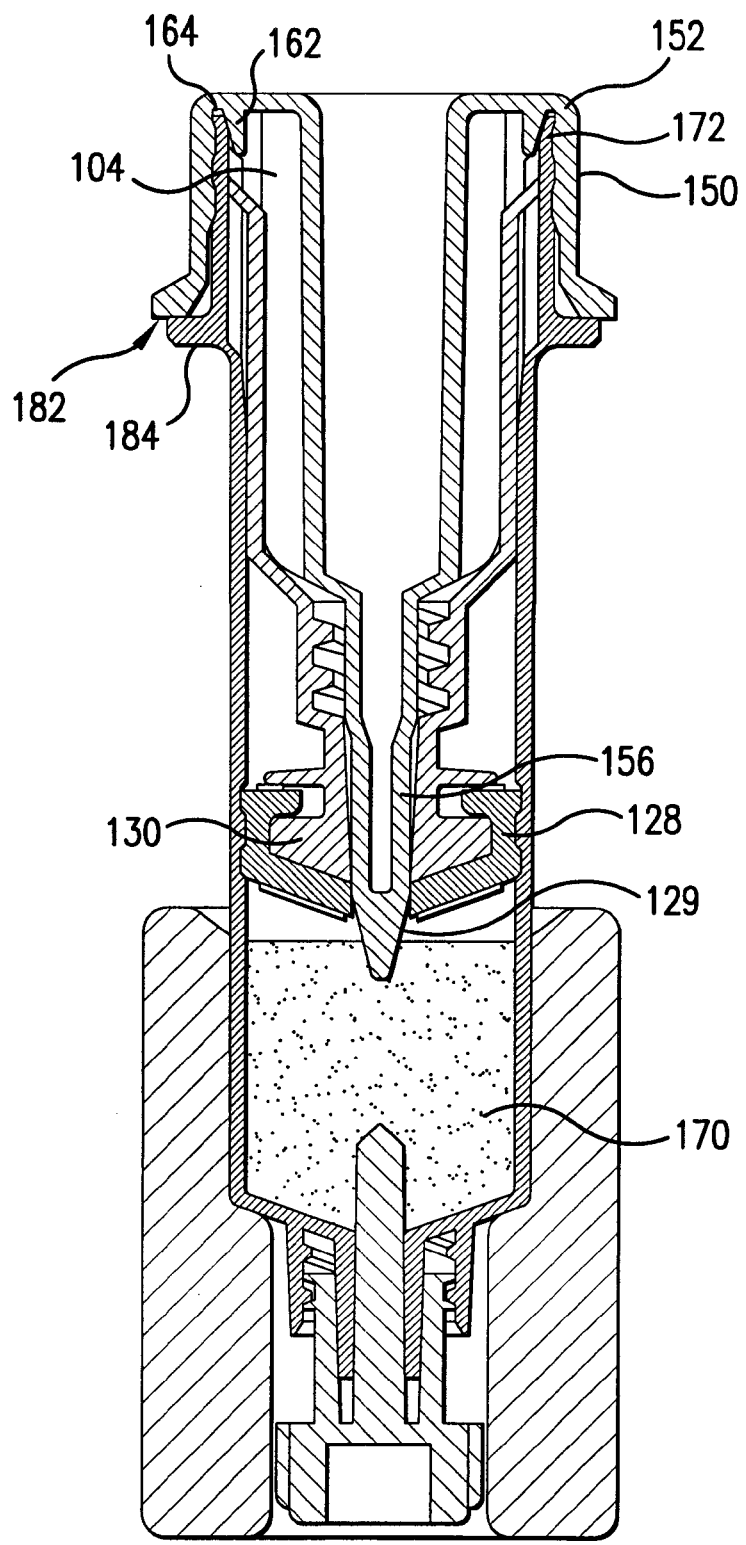
FIG. 8 is a sectional view illustrating the assembly of FIG.7 with the plug cap moved to a sealed position according to the present invention.

FIG. 8 illustrates a step of sealing the venting passage 130 by moving the plug cap 150 into a sealing position. As will be appreciated, movement of the plug cap 150 will typically occur in response to movement of the shelves in the lyophilization chamber. In the sealing position, the occluding tip 156 is disposed within the venting passage 130. In accordance with another aspect of the invention, a lip seal 129 is provided on the stopper 128 to sealingly engage the outer surface of the occluding tip 156. Preferably, the stopper passage 132 is of a dimension such that introduction of the occluding tip 156 into the stopper passage 132 results in deformation outward of the stopper passage 132 such that the lip seal 129 is biased against the occluding tip 156. It will also be recognized that the presence of occluding tip 156 in the venting passage 130 maintains the venting passage in a clear condition, i.e. preventing migration of the lyophilized drug 170 into the venting passage 130 where it might cause interference:between a later inserted diluent syringe (not shown).

As the plug cap 150 is moved to the sealing position illustrated in FIG. 8, the occluding tip 156 provides a seal with the stopper passage 132 to seal the lyophilized drug 171 in the chamber 131. Moreover, the cap portion 152 of the plug cap 150 provides an additional seal as the annular projecting lip 162 of the cap portion extends into the open end 104 of the syringe barrel and the lip 172 of the syringe barrel 102 enters the annular recess 164. Still further, an additional seal is provided between the sealing face 182 on the cap portion 152 and the shoulder 184 on the syringe barrel 102. Finally, an additional seal is provided by the shrink band 184 (FIG. 4) applied around the annular shoulder 184 and the flange 183. Thus, it will be recognized that the exemplary syringe system according to the present invention provides at least four sealing interfaces against contamination of the lyophilized drug 170.

As will be recognized by those of ordinary skill in the art, the present invention provides a syringe system which is capable of being configured into a venting position, that is characterized by a smaller vertical dimension than was previously possible in the prior art. In a typical example, for syringe systems suitable for administering 1 to 3 cubic centimeters of medication, the amount of travel necessary for moving the plug cap from the venting position to a sealing position is no more than about ⅝ of an inch. This is in contrast to the prior art devices which typically required in excess of 1 inch travel for similar capacity syringe systems. Thus, lyophilization chambers configured to operate with syringe systems according to the present invention may be provided with shelves which are closer together and therefore the shelves of the lyophilization chamber may be placed closer together and the capacity of the chamber itself increased so they may accommodate a greater number of syringe systems than was possible in the prior art.

It will also be recognized that the invention provides a more efficient and less restrictive flow path for vapor egress than prior art systems. Thus, the time required for the drying stage of the lyophilization process may be reduced.

It will be readily apparent from the foregoing detailed description of the invention and from the illustrations thereof that numerous variations and modifications may be effected without departing from the true spirit and scope of the novel concepts or principles of this invention, the scope of which is defined in the appended claims.

What is claimed is:

1. A syringe system for containing lyophilized drug, the syringe system comprising:

a syringe barrel including an open end and an opposite dispensing end;

a sterility maintenance sleeve cooperatively associated with the syringe barrel and including a sleeve barrel having an interior-space, the sterility maintenance sleeve including a stopper affixed thereto for sealingly engaging the syringe barrel to define a drug chamber for containing drug solution;

a venting passage in the sterility maintenance sleeve for permitting egress of drug solution vapor from the drug chamber to the interior space when the syringe system is subjected to a lyophilization process; and a plug cap cooperatively associated with the sterility maintenance sleeve and movable from a venting position, in which egress of vapor from the drug chamber to the interior space is permitted, to a sealing position, in which fluid communication between the drug chamber and the interior space is prevented, thereby sealing the drug chamber.

2. The syringe system of claim 1 wherein the sterility maintenance sleeve further comprises a stopper retaining head for retaining the stopper thereon, the venting passage extending through the stopper retaining head.

3. The syringe system of claim 1 wherein the venting passage includes a stopper passage formed in the stopper.

4. The syringe system of claim 1 wherein the plug cap includes an occluding tip for insertion into the venting passage.

5. The syringe system of claim 4 wherein the occluding tip includes a tapered surface.

6. The syringe system of claim 4 wherein the venting passage includes a stopper passage formed in the stopper and a sealing lip formed on the stopper, the sealing lip adapted to sealingly engage the occluding tip.

7. The syringe system of claim 4 wherein the plug cap includes a support structure for supporting the plug cap in the venting position.

8. The syringe system of claim 7 wherein the support structure comprises a plurality of fins extending from the sleeve barrel for engaging the sterility maintenance sleeve.

9. The syringe system of claim 1 wherein the syringe barrel includes a lip around the open end and wherein the plug cap further comprises an annular recess for sealingly engaging the lip.

10. The syringe system of claim 1 wherein the cap plug is adapted to move relative to the sterility maintenance sleeve from the venting position to the sealing position while the sterility maintenance sleeve remains substantially stationary relative to the syringe barrel.

11. The syringe system of claim 1 wherein the plug cap is adapted to travel no more than about $5/8$ of an inch when moving from the venting position to the sealing position.

12. The syringe system of claim 1 wherein the syringe barrel includes a plurality of projections formed integrally with said syringe barrel and located near the open end thereof.

13. The syringe system of claim 12 wherein at least two of said plurality of projections are formed of different lengths.

14. The syringe system of claim 12 wherein the sterility maintenance sleeve includes a plurality of tabs for engaging said projections, said tabs extending radially outward from the sleeve barrel.

15. A method of making a syringe system containing a lyophilized drug, the method comprising:

providing a syringe barrel having an open end and a closed dispensing end;

providing drug solution in the syringe barrel;

inserting a sterility maintenance sleeve into the syringe barrel, the sterility maintenance sleeve including a stopper end defining a venting passage, the stopper end, syringe barrel defining a drug chamber;

inserting a plug cap into the sterility maintenance sleeve;

lyophilizing the drug solution; and sealing the venting passage by moving the plug cap further into the sterility maintenance sleeve.

16. The method of claim 15 wherein the step of moving the plug cap further into the sterility maintenance sleeve comprises moving the plug cap no more than about $5/8$ of an inch.

17. A syringe system made by the method of claim 16.

18. The method of claim 15 wherein the step of sealing the venting passage comprises the step of inserting an occluding tip of the plug cap into the venting passage.

19. A syringe system made by the method of claim 18.

20. The method of claim 15 wherein the step of inserting the sterility maintenance sleeve into the syringe barrel comprises inserting the sterility maintenance sleeve completely into the syringe barrel such that an end of the sterility maintenance sleeve opposite the stopper end is within the syringe barrel.

21. A syringe system made by the method of claim 20.

22. The method of claim 15 wherein the stopper end of the sterility maintenance sleeve is maintained in substantially the same position in the syringe barrel while the step of sealing the venting passage is performed.

23. A syringe system made by the method of claim 22.

24. A syringe system made by the method of claim 15.

25. A syringe system for containing lyophilized drug, the syringe system comprising:

a syringe barrel including an open end and an opposite dispensing end;

a sterility maintenance sleeve disposed within the syringe barrel and including a stopper affixed thereto for sealingly engaging the syringe barrel to define a drug chamber;

a supply of lyophilized drug contained in the drug chamber;

a venting passage in the sterility maintenance sleeve, the venting passage extending from the drug chamber to the interior space; and a plug cap disposed in the sterility maintenance sleeve and including an occluding tip disposed in the venting passage.

26. The syringe system of claim 25 wherein the sterility maintenance sleeve further comprises a stopper retaining head for retaining the stopper thereon, the venting passage extending through the stop retaining head.

27. The syringe system of claim 25 wherein the venting passage includes a stopper passage formed in the stopper.

28. The syringe system of claim 25 wherein the occluding tip includes a tapered surface.

29. The syringe system of claim 25 wherein the venting passage includes a stopper passage formed in the stopper and a sealing lip formed on the stopper, the sealing lip adapted to sealingly engage the occluding tip.

30. The syringe system of claim 25 wherein the plug cap includes a support structure for supporting the plug cap in the venting position.

31. The syringe system of claim 30 wherein the support structure comprises a plurality of fins extending from the sleeve barrel for engaging the sterility maintenance sleeve.

32. The syringe system of claim 25 wherein the syringe barrel includes a lip around the open end and wherein the plug cap further comprises an annular recess for sealingly engaging the lip.

33. The syringe system of claim 25 wherein the syringe barrel includes a plurality of projections formed integrally with said syringe barrel and located near the open end thereof.

34. The syringe system of claim 33 wherein at least two of said plurality of projections are formed of different lengths.

35. The syringe system of claim 34 wherein the sterility maintenance sleeve includes a plurality of tabs for engaging said projections, said tabs extending radially outward from the sleeve barrel.

* * * * *

UNITED STATES PATENT AND TRADEMARK OFFICE
CERTIFICATE OF CORRECTION

PATENT NO. : 6,440,101 B1  
DATED : August 27, 2002  
INVENTOR(S) : Richard W Grabenkort et al.

It is certified that error appears in the above-identified patent and that said Letters Patent is hereby corrected as shown below:

Column 9,
Line 24, replace the term "cap plug" with the term -- plug cap --.

Column 10,
Line 27, replace the word "the" with the word -- an --.
Line 27, after the word "space" insert the phrase -- of the sterility maintenance sleeve --
Lines 45, 47 and 63, replace the word "the" with the word -- a --.

Signed and Sealed this

Sixth Day of May, 2003

JAMES E. ROGAN
*Director of the United States Patent and Trademark Office*